United States Patent [19]

Atrache et al.

[11] Patent Number: 5,415,997
[45] Date of Patent: May 16, 1995

[54] METHOD FOR DETECTING LOW LEVELS OF MICROORGANISMS

[75] Inventors: Vincent H. Atrache, St. Ives; Megan Ash, Hornsby; Ca Van Huynh, Granville, all of Australia

[73] Assignee: Biotechnology Australia PTY Limited, Roseville, Australia

[21] Appl. No.: 196,775

[22] Filed: Feb. 14, 1994

Related U.S. Application Data

[63] Continuation of Ser. No. 2,549, Jan. 11, 1993, abandoned, which is a continuation of Ser. No. 335,787, May 26, 1989, abandoned.

[30] Foreign Application Priority Data

Jul. 28, 1987 [AU] Australia .............................. P13384

[51] Int. Cl.$^6$ .......................................... G01N 33/569
[52] U.S. Cl. ................... 435/7.35; 435/7.32; 435/7.92; 435/29; 435/174; 436/518
[58] Field of Search .................. 435/7.32, 7.2, 7.3, 435/7.35, 7.9, 7.92, 29, 34, 174, 261; 436/518, 524

[56] References Cited

U.S. PATENT DOCUMENTS

| | | | |
|---|---|---|---|
| 3,970,518 | 7/1976 | Giaever | 435/5 |
| 4,563,418 | 7/1986 | Ward, Jr. | 435/7.3 |
| 4,592,994 | 3/1986 | Mattiasson | 435/7.2 |
| 4,677,055 | 6/1987 | Dodin | 435/7.32 |
| 4,683,196 | 7/1987 | McLaughlin | 435/7.32 |

FOREIGN PATENT DOCUMENTS

WO86/04352 7/1986 Australia ............................ 435/176

OTHER PUBLICATIONS

Maggio, E. T., Ed., Enzyme Immunoassay, CRC Press, Inc. Boca Raton, 1980. pp. 167–179.
Rose et al., Manual of Clinical Laboratory Immunology, American Society for Microbiology, Washington, D.C., 1986. pp. 99–109.
Bailey et al., Diagnostic Microbiology. C. V. Mosby Co., St. Louis, 1974. pp. 377, 387, 193–194, 141, 144–147.
Macario, A. J. L., Ed., Monoclonal Antibodies against Bacteria, Academic Press, Orlando, 1985. p. xxii.
Mohit B et al; "A Simple Single-Step Immunoimmobilisation Method for the Detection of Salmonella in the Presence of Large Numbers of Other Bacteria" J Med Microbiol (1975) 8 173–176.
Bulletin OEPP/EEPO Bulletin, vol. 17, 11987, pp. 139–148, Wageningen, NL; J. W. L. Van Vuurde: "New Approach in Detecting Phytopathogenic Bacteria by Combined Immunoidentification Assays".
Van Vuurde et al. (1987) Principles and prospects of new serological techniques including immunosorbent immunofluorescence, immunoaffinity isolation and immunosorbent enrichment for sensitive detection of phytopathogenic bacteria, In Proceedings of the 6th International Conference on Plant Pathogenic Bacteria, Beltsvelle, 1985, Nijhofljunk. the Hague, pp. 835–842.
Hranitzky et al. (1980) Isolation of Ol serovars of *Vibrio cholerae* from water by serologically specific method. Science 210, 1025–1026.
Van Vuurde et al., (1983), Immunosorbent immunofluorescence microscopy (ISIF) and immunosorbent dilution plating (ISPD); new methods for the detection of (List continued on next page.)

Primary Examiner—Esther M. Kepplinger
Assistant Examiner—Donna C. Wortman
Attorney, Agent, or Firm—Foley & Lardner

[57] ABSTRACT

The invention relates to methods for the detection of low numbers of a particular microorganism or microorganisms from a mixed population, the method comprising exposing the sample to a solid support to which antibodies specific for the organism(s) are adsorbed and either growing the bound organism(s) to a detectable level followed by immunoassay or releasing the organisms from the support followed by growth on a nonselective medium and observation of the resultant colonies. The invention also relates to test kits for performing these methods.

18 Claims, No Drawings

OTHER PUBLICATIONS plant pathogenic bacteria. Seed Science. & Technol. II, 523–533.

Van Vuurde et al., (1987), Detecting seedborne bacteria by immunofluorescence. *In Proceedings of the 6th International Conference on Plant Pathogenic Bacteria, Beltsvelle, 1985.* Nijhofljun. The Hague.

Farber, Jeffrey M. and Speirs, Joan L., "Monoclonal Antibodies Directed Against the Flagellar Antigens of Listeria Species and Their Potential in EIA–Based Methods", *Journal of Food Protection,* vol. 50, No. 6, pp. 479–484 (Jun. 1987).

Seeliger, H. and Hohne, K., "Serotyping of Listeria monocytogenes and Related Species", *Methods in Microbiology,* vol. 13, pp. 31–49, (1979).

Paterson, J., Stuart, "Flagellar Antigens of Organisms of the Genus Listerella", Institute of Animal *Pathology,* University of Cambridge, pp. 25–32.

Marfleet, Jane, E., and Blood, Ruth, M., "Listeria Monocytogenes as a Food–Borne Pathogen," *Scientific and Technical Surveys,* No. 157, Feb., 1987.

Lovett, Joseph, "Listeria Isolation", *Bacteriological Analytical Manual,* 6th edition, 1984, chapter 29.

La Roche et al; "Field Evaluation of the Membrane Filter–Disc Immunoimmobilization Technique in the Detection of Salmonellae in Egg Products" Poultry Science (1981) 60 2265–2269.

METHOD FOR DETECTING LOW LEVELS OF MICROORGANISMS

This application is a continuation of application Ser. No. 08/002,549, filed Jan. 11, 1993, now abandoned which is a continuation of Ser. No. 07/335,787, having an International filing date of Jul. 28, 1988 and a 102(e) filing date of May 26, 1989, now abandoned.

TECHNICAL FIELD

The current invention relates to methods for detecting low levels of a particular microorganism, or microorganisms from a mixed culture or sample using antibodies and solid immunosorbent supports without the need for a preliminary or further growth step in selective media.

BACKGROUND ART

Solid-phase immunoassays, based either on enzymes or radioactive isotopes as labels have found wide application in diagnostic microbiology due to their high specificity and sensitivity.

The specificity of an immunoassay is determined by the antibody or antigen which has been immobilized on the solid support. A major advantage of a solid phase assay is that on completion of the immune reaction, unwanted material is easily and rapidly separated from the antigen-antibody immune complex by a simple washing step. A wide variety of solid supports have found application for antibody or antigen immobilization and include polystyrene, polyvinyl chloride, nylon, titanous hydroxide, agarose beads and nitrocellulose.

The successful application of immunoassays to the detection of microorganisms in a sample is possible only if the particular organism of interest is present in sufficient numbers. This critical concentration is determined by the sensitivity of the immunoassay which can vary greatly depending on the affinity and avidity of a particular antibody for its antigen. It is for this reason that many immunoassays require culturing of the sample prior to performing the test.

This usually involves a pre-enrichment step to resuscitate injured microorganisms followed by a selective enrichment to increase the numbers of the microorganism of interest. Selecting culture conditions which favour the growth of a particular microorganism over its competitors has traditionally involved the use of either antibiotics, specific nutritional requirements or manipulation of the physical characteristics of the growth medium, e.g. temperature. These methods can take one to two days or several weeks depending on the organism and the extent of contamination with other microflora.

The use of immunosorbents for selecting microorganisms from a mixed population is known. The sorbent immobilizes a predetermined species of microorganism against which the antibodies are directed. Cells captured in this way can be incubated in a growth medium and then counted by such traditional techniques as plating and colony counting.

U.S. Pat. No. 4,592,994 describes a method for the determination or identification of microorganisms or unicellular organisms in a sample. The method involves exposing the sample to an absorbent having "a specific binding power" which may be provided by an antibody raised against the microorganism to be detected. Unbound sample is separated and the adsorbent with bound organisms is exposed to a nutrient medium to initiate metabolism. This nutrient medium undergoes physical or chemical changes as a result of this metabolism and these changes are observed in conjunction with calibration curves to determine presence and amount of the relevant microorganism. The assay involves indirect detection of original numbers of organisms through detection of metabolites in the medium. This may generate problems with regard to the specificity of the assay since different microorganisms may share metabolites.

U.S. Pat. No. 4,563,418 describes a method for the detection of a particular motile organism in a sample, for example, flagellate bacteria such as Salmonella species.

The method involves enriching the sample in an enrichment medium selective for the particular motile organism and filling a motility vessel with a non-selective medium containing a chemotactic attractant which serves to temporarily immobilize the organism of interest and its competitors in the medium for some time after inoculation. Antibodies specific to the flagella of the particular motile microorganisms are added through another opening in the motility vessel. The vessel is incubated under sufficient temperature and time conditions to permit the motile organisms to metabolize the chemotactic attractant, thereby reducing its concentration sufficiently to allow movement of the organisms present with the result that the organisms move through the medium and the particular motile organisms being assayed are immobilized by the antibodies. The quantity of antibody used is sufficient to produce a permanent immobilization band.

In Mohit et al ["A Simple Single-step Immunoimmobilization Method for the Detection of Salmonella in the Presence of Large Numbers of Other Bacteria" J. Med. Microbiol. 8 173 (1975)], a method of detecting Salmonella in a mixed population is described. This method employs a selective semi-solid medium, which promotes the migration of Salmonella, followed by immobilization using polyvalent H antisera.

La Roche et al in "Field Evaluation of the Membrane Filter-Disc Immobilization Technique in the Detection of Salmonella in Egg Products" describes a method for detecting Salmonella which involves using a membrane filter to concentrate Salmonella from a primary enrichment broth before selective migration in order to increase recovery.

Stannard reported in the annual report for Leatherhead RA for 1986, investigations into separation of Salmonella from other organisms, with a view to reducing the time required for detection of Salmonella in samples.

This method relied on antibody-coated magnetic particles. However, it was found that the apparent enrichment of Salmonella over other closely related organisms was in fact due to differential affinity of these organisms to the glassware used in the experiment. Attempts to use this differential affinity for glass to enrich Salmonella were unsuccessful due to the lack of specificity of the effect.

Thus it can be seen that the prior art methods for detecting microorganisms from mixed populations provide means for detecting low numbers where enrichment in selective medium is used. Immunoimmobilization has been used but has not been shown to be effective for detecting low numbers in the absence of such a selection on selective medium.

The current invention provides methods for detecting low numbers of a particular microorganism or microorganisms in a mixed population which overcome the need for pre-selection in selective media by using an immunoimmobilization technique followed by non-selective growth and immunoassay or by cleavage of the antibody-microorganism bond and growth of the microorganisms on non-selective media.

The methods can be especially usefully applied to detecting Salmonella and Listeria spp meeting the need for rapid, sensitive methods for their detection in mixed populations.

DESCRIPTION OF THE INVENTION

The invention provides methods for the rapid detection of a particular microorganism, or microorganisms, in the presence of competing micro-flora using specific antibodies adsorbed onto a solid support. The immobilized antibody is to an antigen of the microorganism which allows selective capture and immobilization of the desired microorganism without compromising its ability to replicate. Appropriate antibodies can be raised against surface antigens provided by such surface structures as flagella or lipopolysaccharides. Selective concentration of the desired microorganism or microorganisms onto the solid support allows rapid separation from competing microflora in the sample and is achieved by simply washing the solid support. The immobilized cells can then be transferred to a nutrient broth to allow replication during which time the multiplying microorganisms will continue to be captured and immobilized on the solid support until the antibody sites are saturated.

The time taken for the concentration of the microorganisms to reach a detectable level will depend on the generation time of the particular microorganism or microorganisms and on the sensitivity limits of the immunoassay.

Once a detectable level is reached the solid support is simply separated from the culture broth, then washed and assayed directly.

Alternatively, the antibody-microorganism bond can be broken by an appropriate agent resulting in the release of the microorganism. The released cells can be transferred to a nutrient medium to allow replication and detection of colonies that form.

The selection of the microorganism or microorganisms during the immuncimmobilization step can involve selection of surface antigens that are common to a genus, to a particular species within that genus or if very high selectivity is required, antigens that are specific to a serotype of that species may be chosen.

This technique thus aliminates the need for elaborate and expensive enrichment media in providing rapid sensitive detection of low levels of a particular microorganism or microorganisms from mixed populations.

In a first embodiment, the invention provides a method for detecting low levels of a particular microorganism or microorganisms in the presence of competing microflora in a sample which method comprises: exposing the sample to a solid support to which are adsorbed antibodies specific for the microorganism or microorganisms being detected, said antibodies being capable of selective capture and immobilisation of the microorganism or microorganisms without compromising the ability of the microorganism or microorganisms to replicate; washing the support to remove unbound materials; adding sterile nutrient broth to the support; incubating the support in the nutrient broth at a temperature and for a time relative to the generation time of the microorganism or microorganisms sufficient to allow the microorganism or microorganisms to reach a detectable level; washing the support and then performing an immunoassay on the support using an immunoreagent specific for the microorganism or microorganisms being detected.

Preferably the antibody is raised against a surface antigen of the microorganism. More preferably the surface antigen is a flagellar protein or lipopolysaccharide.

In a preferred form, the antibodies are immobilized onto a solid support comprising a bead, tube or well.

Preferably, the support material is polystyrene, polyvinyl chloride, nylon, titanous hydroxide, agarose beads or nitrocellulose.

Preferred microorganisms, according to the invention include Salmonella species and Listeria species.

The exposure of the sample to the antibody-coated support is generally for 1 hour or less. The wash steps are preferably performed using sterile saline buffer, more preferably Tris-saline buffer. Virtually any nutrient broth may be used in the method, however, preferred broths are tryptone soya broth and M broth. The incubation in nutrient medium may be overnight and is usually at 37° C. However, for detection of Salmonella typhimurium, incubation times of approximately 6 hours have been shown to be effective. Where higher numbers of the particular microorganism are present in the original sample incubation times of between 1 and 6 hours can be used. Preferably, the immunoassay is an ELISA.

In a more preferred form the method comprises; exposing a Salmonella test sample for between about 5 and about 30 minutes to a polystyrene support to which are adsorbed anti-Salmonella flagella antibodies, said antibodies being capable of selective capture and immobilisation of Salmonella without compromising the ability of the Salmonella to replicate; washing the support to remove unbound material; adding sterile nutrient broth to the support; incubating the support at 37° C. for between about 1 and about 6 hours; washing the support; adding an enzyme-labelled antibody specific to Salmonella; incubating for between about 5 and about 30 minutes: discarding any excess enzyme-labelled antibody; washing the support; adding a chromogenic substrate specific for the enzyme of the enzyme-labelled antibody; and measuring conversion of the chromogenic substrate to a coloured compound.

Preferably the support is a tube, bead or microtitre well.

Preferably the enzyme-labelled antibody is an (anti-Salmonella) antibody-peroxidase conjugate. However, it is recognised that it is possible to use an unlabelled anti-Salmonella antibody in conjunction with a labelled antibody raised against the anti-Salmonella antibody in an indirect version of the assay for bound Salmonella.

Preferably the wash is performed using a Tris-saline solution as wash solution.

Preferably the substrate is an ABTS/$H_2O_2$ solution.

Preferably the nutrient broth is tryptone soya broth.

In a second embodiment the invention provides a method for detecting low levels of a particular microorganism or microorganisms in the presence of competing microflora in a sample which method comprises: exposing the sample to a solid support to which are adsorbed antibodies specific for the microorganism or microorganisms, said antibodies being capable of selective capture and immobilisation of the microorganism or microorganisms without compromising the ability of the microorganism or microorganisms to replicate; washing the support to remove unbound material; releasing the bound microorganism or microorganisms with a releasing agent; adding the released material to a nutrient medium; and incubating at a temperature and for a time relative to the generation time of the microorganism or microorganisms being detected to allow the microorganism or microorganisms to reach a detectable level.

Releasing agents suitable for dissociating the antibody-microorganism bond include:
1) chaotropic agents such as 4.5M $MgCl_2$ pH 7.5 or 2.5M NaI pH 7.5
2) polarity reducing agents such as ethylene glycol in solutions of up to 50%.
3) pH change inducing agents such as glycine/HCl pH 2.5, aqueous $NH_3$ pH 11 or 0.5% KOH pH 12.5.

Preferably the releasing agent is 0.5% KOH pH 12.5. To this solution protein may be added to provide a carrier for the released microorganisms.

In a preferred form the microorganisms are Listeria species or Salmonella species, more preferably *Listeria monocytogenes*.

It is recognised that prior to the release of the bound microorganisms they may also be subjected to a non-selective growth in nutrient medium to increase their numbers prior to release and detection.

The sample is preferably exposed to the antibody coated support for approximately 5 minutes. The wash solution is preferably a sterile saline solution, more preferably sterile Tris-HCl buffered saline pH 7.5. Virtually any nutrient medium may be used, however, Trypticase tryptone soya broth soya agar is a preferred medium. The plates are preferably incubated at 37° for between 18 and 24 hours. By using nutient medium in place of selective media incubation can be reduced to as short a time as 12 hours.

In a more preferred form the method comprises: exposing a Listeria test sample for about 5 minutes to a polystyrene support to which are adsorbed antibodies specific to Listeria species, said antibodies being capable of selective capture and immobilisation of Listeria species without compromising the ability of the Listeria species to replicate; washing the support to remove unbound material; releasing the bound Listeria with a releasing agent; adding the released material to a nutrient agar plate; and incubating the plate for about 16–18 hours at 37° C.

Preferably the antibodies are (anti-Listeria flagella) antibodies.

Preferably the releasing agent is a 0.5% KOH solution.

Preferably washing is performed using a Tris/Saline pH 7.5 solution.

Preferably the nutrient agar plate is a trypticase soya agar plate.

The invention also provides a test kit for the detection of low levels of a particular microorganism or microorganisms in a mixed population which kit comprises; a solid support to which are adsorbed antibodies specific for the microorganism or microrganisms being detected; a wash solution; an enzyme-labelled antibody specific for the microorganism or microorganisms being detected; and a solution of a chromogenic substrate for the enzyme of the enzyme-labelled antibody.

In place of the enzyme-labelled antibody the kit may comprise an anti-microorganism antibody together with an enzyme-labelled antibody raised against the anti-microorganism antibody.

The invention also provides a test kit comprising: a solid support to which are adsorbed antibodies specific for the microorganism or microorganisms being detected; a releasing agent; and a wash solution.

BEST METHOD OF PERFORMING THE INVENTION

The invention is further described with reference to the following examples which are in no way limiting on the scope of the invention.

EXAMPLE 1

Selective isolation of salmonella using antibody coated wells

*Salmonella typhimurium* (inhouse strain BTA 438) and *Citrobacter diversus* (BTA 1323) were inoculated into individual M broth solutions and were incubated overnight at 37° C. Each of the cultures grew to $10^9$ organisms/ml. These were then diluted as follows:

$10^8$ cells/ml *C. diversus* with $10^4$ cells/ml *S. typhimurium*

$10^8$ cells/ml *C. diversus* with $10^3$ cells/ml *S. typhimurium*

$10^8$ cells/ml *C. diversus* with $10^2$ cells/ml *S. typhimurium*

$10^8$ cells/ml *C. diversus* with $10^1$ cells/ml *S. typhimurium*

$10^8$ cells/ml *C. diversus* with $10^0$ cells/ml *S. typhimurium*

$10^8$ cells/ml *C. diversus* only (control)

Polystyrene wells coated with highly purified antibodies to Salmonella flagella were then added to the M broths containing the mixed cultures. Wells coated with non-immune sheep immunoglobulin were placed into a duplicate set of mixed cultures as a control. The broths containing the wells were shaken for 1 hour at 37° C.

The wells were then carefully removed and washed 3 times in Tris-saline, then placed in fresh M broth solutions. These M broths were incubated overnight at 37° C. to allow the immobilised organisms to multiply. The wells were then removed from the M broths and an ELISA was performed on them.

EIA Method

The wells were washed three times with Tris-saline-Tween (TST) polyoxyethylene (20) sorbitol monolaurate then anti-Salmonella IgG-Horseradish Peroxidase labelled conjugate was added. After 30 minutes incubation at 37° C., the wells were washed three times with TST, then substrate (2,2-azinobis(3-ethylbenzthiazoline sulfonic acid)) in citrate-phosphate buffer (0.1M, pH4) containing hydrogen peroxide (0.005%) was added and colour allowed to develop.

| ORGANISMS/ML | | OPTICAL DENSITY[1] | |
|---|---|---|---|
| C. diversus | S. typhimurium | Salmonella Ab Coated Wells | Control Wells[2] |
| $10^8$ | + | $10^4$ | 2.0 | 0.026 |
| $10^8$ | + | $10^3$ | 1.378 | 0.035 |
| $10^8$ | + | $10^2$ | 0.306 | 0.063 |
| $10^8$ | + | $10^1$ | 0.314 | 0.042 |
| $10^8$ | + | $10^0$ | 0.066 | 0.050 |
| $10^8$ | | | 0.078 | 0.037 |

[1] Optical densities read using dual wavelength ELISA reader at 414 nm and 490 nm.
[2] Non-immune sheep immunoglobulin coated wells.

EXAMPLE 2

The method was compared with the Standard Culture Enrichment protocol [AOAC Official Methods of Analysis 963-971 (1984)] and showed increased speed of performance, and enhanced selectivity and sensitivity as described below.

The protocol was as described in Example 1 except that 1 ml of the M broth containing the mixed cultures was placed into 10 ml of tetrathionate broth and incubated at 37° C. for 6 hours.

Following this, an ELISA was performed on the broths. To the remaining 9 ml of broth, wells coated with highly purified antibodies to Salmonella flagella were added and the procedure of Example 1 followed except that the incubation of the M broth was for 6 hours only and then an ELISA was performed.

| ORGANISMS/ML | | OPTICAL DENSITY[1] | |
|---|---|---|---|
| C. DIVERSUS | S. TYPHIMURIUM | SALMONELLA Ab COATED WELLS | TETRATHIONATE BROTHS |
| $10^8$ | + $10^4$ | 2.0 | 0.113 |
| $10^8$ | + $10^3$ | 2.0 | 0.089 |
| $10^8$ | + $10^2$ | 0.244 | 0.076 |
| $10^8$ | + $10^1$ | 0.200 | 0.061 |
| $10^8$ | control | 0.030 | 0.065 |

[1]Optical densities read using dual wavelength ELISA reader at 414 nm and 490 nm.

After 6 hours the ELISA detected $10^3$ Salmonella in the presence of $10^6$ Citrobacter from the coated wells whilst after 6 hours selective enrichment in tetrathionate no Salmonella were detected by the ELISA.

EXAMPLE 3

Selective isolation of Listeria monocytogenes from mixed cultures

*Listeria monocytogenes* (BTA No. 1767). *Staphylococcus aureus* (BTA No. 1414), and *Streptococcus faecalis* (ATCC No. 19433) were individually cultured in Tryptose-Soya broth overnight at 28° C. Each of the cultures grew to a minimum of $10^9$ organisms/ml and were then diluted and mixed as follows:

| | |
|---|---|
| Mixture A: | $10^9$ cells/ml *Staphylococcus aureus* + $10^6$ cells/ml *L. monocytogenes.* |
| Mixture B: | $10^9$ cells/ml *Streptococcus faecalis* + $10^6$ cells/ml *L. monocytogenes.* |
| Controls: | $10^9$ cells/ml *S. faecalis* |
| | $10^9$ cells/ml *S. aureus* |
| | $10^6$ cells/ml *L. monocytogenes* |

A 200 µl sample from each of the above cultures was incubated in a polystyrene well, precoated with highly purified antibodies to Listeria flagella. After 5 minutes incubation at room temperature the wells were emptied and washed three times with sterile Tris-HCl buffered saline pH 7.5. Any captured organisms were then released into solution by the addition of 0.5% KOH solution pH 12.5 (100 µl) and immediately transferred to Tryptose Soya Agar plates and spread using a glass spreader. For comparative purposes each of the cultures above was also examined directly without immunoenrichment by streaking a 10 µl aliquot onto Tryptose Soya Agar. All plates were incubated for 18-24 hours at 37° C. and then examined under oblique light for typical colonies of *Listeria monocytogenes* (sparkling bluish-grey, translucent, 0.5-1.5 mm in diameter, watery consistency).

| RESULTS | | | | |
|---|---|---|---|---|
| | Colonies Counted | | | |
| | Immuno-enrichment | | Direct Plating | |
| Sample Tested | Listeria | Other | Listeria | Other |
| Mixture A | 253 | 222 | 0 | >1000 |
| Mixture B | 125 | 264 | 0 | >1000 |
| *S. aureus* $10^9$ cells/ml | — | 246 | — | >1000 |
| *S. faecalis* $10^9$ cells/ml | — | 500 | — | >1000 |
| *L. monocytogenes* $10^6$ cells/ml | 127 | — | >1000 | — |

In a single step, approximately a one thousand fold enrichment of *L. monocytogenes* over the competing microorganism was achieved. Isolation was greatly simplified and detection was possible when direct plating of such a mixture failed to isolate a Listeria colony.

EXAMPLE 4

Sensitivity of Immunoenrichment for the isolation of Listeria monocytogenes

*Listeria monocytogenes* was cultured in Tryptose Soya Broth for 18 hours at 28° C. The culture was then diluted in sterile saline to give concentrations of $10^7$, $10^6$, $10^5$ and $10^4$ organisms/ml. Samples (200 µl) of each dilution, tested in triplicate, were incubated in individual anti-Listeria antibody coated wells for 5 minutes then the wells emptied and washed with sterile buffered saline pH 7.5. Any immobilized microorganisms were released into solution by the addition of 0.5% KOH solution pH 12.5 and then immediately transferred to tryptose Soya Agar plates and spread using a glass spreader. Plates were incubated at 37° C. for 18-24 hours and the number of colonies counted.

| RESULTS | |
|---|---|
| Number of organisms added/well | No. of Colonies counted |
| $2 \times 10^6$ | 1000 |
| $2 \times 10^5$ | 300 |
| $2 \times 10^4$ | 50 |
| $2 \times 10^3$ | 1 |

Sensitivity of the method allowed detection of *Listeria monocytogenes* when as few as $2 \times 10^3$ organisms were incubated in the antibody coated well.

EXAMPLE 5

General Method:

A Listeria test sample was adjusted to pH 7.5-8.0 and 200 µl were transferred into a U.S.A. Dynatech Removawell TM which has been coated with anti-Listeria antibodies in 10 mm phosphate buffer pH 8.1, 10 µg/ml O/N at 20°-25° C.

The sample was incubated at room temperature for 5 minutes.

The well was then washed gently with sterile Tris-Saline solution at pH 7.5.

100 μl of KOH (pH 11.1) was added.

A 100 μl aliquot of the resulting KOH mix was transferred to a Tryptone soya agar or modified McBride agar plate and spread using a glass spreader. The plate was incubated for between 18 and 24 hours at 37° C. and the plate examined for typical Listeria colonies.

Optimization of reaction time for immunoenrichment

Culture: *Listeria monocytogenes* (BTA 1767) was grown in OXOID's TSO+0.6% yeast extract at 28° C. overnight.
Releasing reagent: 0.5% KOH (pH 10.5).
Plate: Modified McBride Agar plate.

| Microorganisms | No. of Listeria colonies isolated on MMA plate | | | | |
|---|---|---|---|---|---|
| | 5 min. | 10 min. | 15 min. | 20 min | 30 min. |
| *$10^5$ cells/ml of L. m. | 58 | 54 | 37 | 7 | 15 |
| *$10^5$ cells/ml of L. m. +$10^9$ cell/ml *Streptococcus faecalis* | 100 | 110 | 84 | — | 10 |

Immuno-enrichment for Listeria using different releasing reagents

| *Listeria monocytogenes* dilution | Releasing reagent | No. of colonies on TSA plate |
|---|---|---|
| ($2 \times 10^6$ cell/ml) | 0.01% KOH + 0.85% NaCl | 145 |
| " | " | 149 |
| ($2 \times 10^6$ cell/ml) | 0.01% NaOH + 0.85% NaCl | 191 |
| " | " | 260 |
| ($10^6$ cell/ml) | 0.01% KOH + 0.85% NaCl | 122 |
| " | 0.01% NaOH + 0.85% NaCl | 145 |
| " | " | 118 |
| " | 10 mM Tris (pH 11.1) + 0.85% NaCl | 112 |
| " | 10 mM Tris (pH 11.1) + 0.85% NaCl | 161 |

| *Listeria Innocua* (CT-94) | Releasing reagent | No. of colonies on TSA plates |
|---|---|---|
| " | 0.01% KOH + 0.85% NaCl | 58 |
| " | " | 65 |
| ($10^6$ cell/ml) | 0.1M $Na_2CO_3$ (pH 11.1) | 163 |
| " | " | 126 |

Specificity of Immunoenrichment (1) Culture: All cultures were grown in OXOID's TSB at 28° C. overnight.
Releasing reagent: 0.01% KOH + 0.85% NaCl (pH 11.1)
Microtitre wells: Listeria antibody coated wells.
Staphylococcus exterotoxin antibody coated well.
Blank well (normal gamma irradiated polystyrene well).

| Mixture of microorganisms | Type of well | No. of Listeria on TSA plate |
|---|---|---|
| *$10^8$ cell/ml *L. monocytogenes* + $10^8$ cell/ml of Rhodococcus equi + $10^9$ cell/ml Staphylococcus | Listeria antibody coated well | 2.000–3.000 |
| | | 2.000–3.000 |
| *The same mixture as above | Staphylococcus exterotoxin antibody coated well | 0 |
| | | 0 |
| *The same mixture as above | Blank well | 0 |
| | | 1 |

EXAMPLE 6

Salmonella Rapid Detection Kit

This kit enables the user to rapidly test for the presence of Salmonella in food, environmental or clinical samples. Highly specific antibodies to Salmonella flagella coated onto the surface of polystyrene tubes are used to capture Salmonella organisms present in a test sample. This is achieved by incubating the test sample in the antibody coated tube for a short time e.g.: 5–30 minutes. The tube is then washed thoroughly to remove unbound material. Sterile nutrient broth e.g: Tryptone soya broth is then added and the tube incubated at 37° C. for 1–6 h. During this time the immobilised Salmonella replicate and continue to be captured by available antibodies on the tube surface. This allows for a sufficient concentration of organisms to be reached for subsequent detection by immunoassay.

The presence of the captured organisms can now be detected by discarding the culture broth and then adding an enzyme-labelled antibody specific to Salmonella. After a short incubation (5–30 min) excess enzyme-antibody reagent is discarded and the tube washed.

The enzyme-antibody conjugate which has specifically bound to the immobilised organisms is detected by addition of a substrate for the enzyme.

Materials Provided anti-Salmonella antibody coated polystyrene tubes
anti-Salmonella-antibody-Peroxidase conjugate
wash solution Tris Saline Tween polyoxyethylene (20) sorbitol monolaurate
Substrate solution-ABTS/$H_2O_2$ By use of Listeria reagents in the place of the Salmonella reagents this kit can be adapted to the detection of Listeria.

Listeria Detection Kit

The kit allows the selective isolation of Listeria from culture broths derived from either food or environmental samples and eliminates the need to develop/use selective agar plates for the isolation of the organism.

Highly specific antibodies to Listeria are immobilised on the internal surface of polystyrene tubes provided. An aliquot of the test solution is incubated in the antibody coated tube for a specified time (5 minutes). The tube is then emptied and washed to remove unbound material. Any captured Listeria is then released by the addition of a releasing agent e.g. 0.5% KOH solution. The Listeria released into solution are spread onto a nutrient agar e.g. Trypticase soya agar and the plate incubated for 16–18 hours at 37° C. to allow the organisms to replicate.

By this procedure the desired organism is readily isolated from an initial culture broth, (sample) contaminated with a variety of other organisms and thus obviates the need for selective agars. In the specific case of Listeria the described method shows superior selectively over the selective agars currently recommended by the Microbiological Standard Methods.

Materials Provided (1) Anti-Listeria flagella antibody coated polystyrene tubes
(2) Releasing agent (0.5% KOH solution)
(3) Wash Buffer Tris/Saline pH 7.5

By replacing the Listeria reagents with Salmonella reagents this kit can be adapted to the detection of Salmonella.

These examples illustrate the usefulness of these methods for the rapid detection of a specific organism in a mixed culture.

The methods are more rapid than traditional culture enrichment protocols, with a positive result being obtainable as rapidly as 6 hours, compared to a minimum of 48 hours by standard culture methods.

Industrial Application

The current invention provides an alternative to use of specialized selection media for the detection of low numbers of a particular microorganism or microorganisms in a mixed population.

We claim:

1. A method for the detection in a sample, in the presence of competing microflora, of low levels of a particular microorganism selected from the group consisting of a genus, a species and a serotype, which method comprises:
   (i) exposing said sample to a solid support to which are adsorbed antibodies specific for said microorganism;
   (ii) washing said solid support to remove unbound material;
   (iii) combining said solid support with sterile nutrient broth which permits replication of said microorganism;
   (iv) incubating said solid support with said nutrient broth at a temperature and for a time sufficient to allow said microorganism to replicate and be recaptured by said antibodies on said solid support, whereby a detectable level of said microorganism on said solid support is reached;
   (v) washing said solid support; and
   (vi) performing an immunoassay on said solid support using an immunoreagent specific for said microorganism and thereby detecting said microorganism.

2. The method according to claim 1, wherein said antibodies are specific for a surface antigen of said microorganism.

3. The method according to claim 2, wherein said surface antigen is a flagellar protein or lipopolysaccharide.

4. The method according to claim 1, wherein said solid support is selected from the group consisting of a bead, a tube and a well.

5. The method according to claim 1, wherein said solid support is made of a material selected from the group consisting of polystyrene, polyvinyl chloride, nylon, titanous hydroxide, agarose and nitrocellulose.

6. The method according to claim 1, wherein said microorganism is a Salmonella species or a Listeria species.

7. The method according to claim 1, wherein said sample is exposed to said solid support for no more than one hour.

8. The method according to claim 1, wherein said nutrient broth is selected from the group consisting of tryptone soya broth and M broth.

9. The method according to claim 1, wherein said incubation in nutrient broth is at 37° C. for 6 hours.

10. The method according to claim 1, wherein said immunoassay is an ELISA.

11. The method according to claim 10, wherein said immunoreagent is an enzyme-labeled, anti-microorganism antibody.

12. The method according to claim 10, wherein said immunoreagent comprises an anti-microorganism antibody and an enzyme-labeled antibody specific for said anti-microorganism antibody.

13. The method according to claim 1, wherein said microorganism is a Salmonella species, said solid support is made of polystyrene, said exposing takes place for about 5 to 30 minutes, said adsorbed antibodies are anti-Salmonella flagella antibodies, said incubating occurs at 37° C. for about 1 to 6 hours, and said immunoreagent is an enzyme-labeled antibody specific to Salmonella.

14. The method according to claim 1, wherein said immunoassay of step (vi) comprises the steps of
   (a) incubating said solid support with said enzyme-labeled antibody for a period of between about 5 minutes and 30 minutes;
   (b) washing said solid support with a wash solution;
   (c) adding to said solid support a chromogenic substrate specific for the enzyme of said enzyme-labeled antibody;
   (d) measuring conversion of said chromogenic substrate to a colored enzyme product; and
   (e) comparing said conversion with a standard.

15. The method according to claim 14, wherein said solid support is selected from the group consisting of a tube, a bead and a microtiter well.

16. The method according to claim 14, wherein the enzyme of said enzyme-labeled antibody is a peroxidase.

17. The method according to claim 14, wherein said substrate is a solution of 2,2-azinobis(3-foethylbenzthiazoline sulfonic acid)), in ABTS in citrate buffer containing hydrogen peroxide.

18. The method according to claim 17, wherein said nutrient broth is tryptone soya broth.

* * * * *

UNITED STATES PATENT AND TRADEMARK OFFICE
CERTIFICATE OF CORRECTION

PATENT NO. : 5,415,997
DATED : May 16, 1995
INVENTOR(S) : Vincent H. ATRACHE et al.

It is certified that error appears in the above-indentified patent and that said Letters Patent is hereby corrected as shown below:

Column 12, line 49, Claim 17, contains a typographical error wherein "3-foethylbenz-" should read --3-ethylbenz---;

Column 12, line 50, Claim 17, "acid)), in ABTS" should read --acid), ABTS,--.

Signed and Sealed this

Fifth Day of December, 1995

Attest:

BRUCE LEHMAN

*Attesting Officer*     Commissioner of Patents and Trademarks